(12) United States Patent
Works et al.

(10) Patent No.: US 8,962,036 B2
(45) Date of Patent: Feb. 24, 2015

(54) DISINTEGRABLE FORMULATIONS OF LANTHANUM CARBONATE

(75) Inventors: Andrea Blum Works, Morgantown, WV (US); John Twist, Morgantown, WV (US); Okey Noe, Morgantown, WV (US)

(73) Assignee: Mylan Pharmaceuticals Inc., Morgantown, WV (US)

( * ) Notice: Subject to any disclaimer, the term of this patent is extended or adjusted under 35 U.S.C. 154(b) by 480 days.

(21) Appl. No.: 13/145,589

(22) PCT Filed: Jan. 21, 2010

(86) PCT No.: PCT/US2010/021573
§ 371 (c)(1),
(2), (4) Date: Jul. 21, 2011

(87) PCT Pub. No.: WO2010/085520
PCT Pub. Date: Jul. 29, 2010

(65) Prior Publication Data
US 2011/0280967 A1    Nov. 17, 2011

Related U.S. Application Data

(60) Provisional application No. 61/146,162, filed on Jan. 21, 2009.

(51) Int. Cl.
| | |
|---|---|
| *A61K 33/24* | (2006.01) |
| *A61K 47/02* | (2006.01) |
| *A61K 47/10* | (2006.01) |
| *A61K 47/32* | (2006.01) |
| *A61K 47/36* | (2006.01) |
| *A61P 3/12* | (2006.01) |
| *A61K 9/00* | (2006.01) |
| *A61K 9/20* | (2006.01) |
| *A61K 9/16* | (2006.01) |
| *A61K 9/19* | (2006.01) |

(52) U.S. Cl.
CPC ............... *A61K 33/24* (2013.01); *A61K 9/0056* (2013.01); *A61K 9/2009* (2013.01); *A61K 9/2018* (2013.01); *A61K 9/2095* (2013.01); *A61K 9/1623* (2013.01); *A61K 9/19* (2013.01)
USPC .......... 424/600; 424/715; 514/770; 514/772.5; 514/777; 514/778

(58) Field of Classification Search
None
See application file for complete search history.

(56) References Cited

U.S. PATENT DOCUMENTS

| | | | |
|---|---|---|---|
| 5,618,772 A | 4/1997 | Suda et al. | |
| 5,968,976 A * | 10/1999 | Murrer et al. | ................. 514/492 |
| 7,465,465 B2 | 12/2008 | Haslam et al. | |
| 2004/0254210 A1* | 12/2004 | Haeberlin et al. | ............ 514/291 |
| 2006/0003018 A1 | 1/2006 | Moerck et al. | |

FOREIGN PATENT DOCUMENTS

WO    WO 2008000453 A2 *    1/2008

OTHER PUBLICATIONS

"Excipients", Wikipedia (2013).*
International Search Report dated Mar. 12, 2010 issued for WO 2010/085520.

* cited by examiner

*Primary Examiner* — Abigail Fisher
*Assistant Examiner* — Frank Choi

(57) ABSTRACT

Disintegrable preparations of lanthanum carbonate prepared by co-precipitation, facilitating the manufacture of oral pharmaceutical dosage forms such as tablets, capsules, powders, granules, and sprinkles, and the use of such dosage forms to treat subjects with hyperphosphatemia are disclosed.

23 Claims, No Drawings

DISINTEGRABLE FORMULATIONS OF LANTHANUM CARBONATE

FIELD OF THE INVENTION

This invention relates to stable, disintegrable preparations of lanthanum carbonate which facilitate pharmaceutical oral solid dosage forms such as tablets, capsules, granules, powders, and sprinkles and the use of such dosage forms to treat subjects with hyperphosphatemia.

BACKGROUND OF THE INVENTION

Hyperphosphatemia occurs when the blood stores high levels of inorganic phosphate. This condition is prevalent in patients with severe kidney dysfunction, including chronic renal insufficiency and end stage renal disease. Similar to calcium, phosphate is found in bones and teeth and absorption occurs efficiently with consistent Vitamin D intake. Under normal conditions, the kidneys excrete phosphate. However in those patients with hyperphosphatemia, the kidneys are unable to remove the phosphate and dialysis proves to be ineffective in phosphate removal.

Patents with hyperphosphatemia often do not exhibit symptoms. Progressive bone weakness can occur however, resulting in pain and the bone's increased susceptibility to fractures and breaks. Phosphate that crystallizes in the walls of blood vessels and the heart can cause arteriosclerosis and lead to strokes, heart attacks, and poor circulation. Skin sensitivity can also occur if these phosphate crystals form in the skin.

Lanthanum carbonate is a known phosphate binder and is used to reduce phosphate levels in patients with hyperphosphatemia, and specifically, those patients with hyperphosphatemia caused by end stage renal disease. Reduction of serum phosphate and calcium phosphate is accomplished through lanthanum carbonate's inhibition of phosphate absorption through formation of insoluble lanthanum phosphate complexes. Furthermore, there has been a recent push to expand the labeled use of the phosphate binder to include the treatment of hyperphosphatemia in stage 4 chronic kidney disease patients. In October of 2007, the U.S. Food and Drug Administration's Cardiovascular and Renal Drugs Advisory Committee recommended the extension to include this broader use.

Lanthanum carbonate is currently available from Shire US Inc. in 500, 750, and 1000 mg chewable tablets, marketed under the trade name, Fosrenol®. The chewable tablets are the only dosage form available for patients. When placed in water, these tablets do not disintegrate, but remain as large granules, even after a period of many hours. The Fosrenol® chewable tablets are of substantial size, ranging in diameter from 18 mm for the 500 mg strength and 22 mm for the 1000 mg strength. Chewable tablets are often not ideal, as they can be difficult for patients to ingest and often have an unpleasant taste. Further, many patients, children and elderly in particular, often display difficulty in chewing such tablets thoroughly, leading to an inadequate therapeutic delivery. Phosphate uptake is dependent upon the surface area of the insoluble lanthanum carbonate particles. The surface area of the lanthanum carbonate depends upon the thoroughness of the patient's chewing, resulting in a wide variance of effectiveness of the actual ingested dose of active lanthanum carbonate. Therefore, increased dosages of Fosrenol® are often necessary to obtain effective levels of lanthanum carbonate.

U.S. Pat. No. 5,968,976 discloses a pharmaceutical composition for treating hyperphosphatemia comprised of lanthanum carbonate of the formula $La_2(CO_3)_3 \cdot xH_2O$, where x has a value from 3 to 6, in admixture with a pharmaceutically acceptable diluent or carrier, in a form for administration to the gastrointestinal tract. A process for its preparation is also disclosed and comprises oven drying lanthanum carbonate octahydrate to obtain the lanthanum carbonate with 3 to 6 moles of water. The patent does not disclose adequate means of oral delivery of the lanthanum carbonate for effective compliance and therapeutic delivery.

U.S. Pat. No. 7,381,428 discloses a method for treating hyperphosphatemia with a formulation comprising a lanthanum carbonate composition of $La_2(CO_3)_3 \cdot xH_2O$, wherein x equals between 0 and 10, and at least one monosaccharide or disaccharide stabilizer to stabilize the lanthanum carbonate against decarboxylation to lanthanum hydroxycarbonate. The patent does not disclose adequate means of oral delivery of the lanthanum carbonate for effective compliance and therapeutic delivery.

U.S. Pat. No. 7,465,465 discloses a chewable lanthanum formulation in a tablet comprising lanthanum and a chewable excipient. This application further discloses the lanthanum tablet formulation produced through a process of powder blending the lanthanum compound and an excipient in a mixer to form a mixture. The mixture is then either compressing into a slug material or roller compacting into a strand material. The compressed/compacted material is then milled into a free flowing mixture and compressed into a tablet. These formulations have the disclosed use of treatment for hyperphosphatemia. This representation of the current state of the art does not address the insufficiencies of these chewable tablets in patient compliance and therapeutic delivery.

United States Patent Application Publication Nos. 2004/0161474, 2006/0003018, 2006/0083791, and 2008/0226735 disclose lanthanum carbonate preparations with specific surface area to increase phosphate binding ability. The applications do not address suitable dosage forms to allow for better patient compliance and therapeutic delivery.

United States Patent Application Publication No. 2005/0208080 discloses a formulation of lanthanum carbonate in the form of a sandwich biscuit. This "cookie" has two or more layers that support an unpalatable medicament, i.e. lanthanum carbonate. The application, however, does not disclose a method of improving the phosphate binding of the lanthanum carbonate.

The current state of lanthanum carbonate pharmaceutical dosage forms are not sufficient. The considerable size of the chew tablets coupled with their unpleasant taste lead to poor patient compliance and inadequate therapeutic delivery.

SUMMARY OF THE INVENTION

A need remains for new pharmaceutical dosage forms of lanthanum carbonate. Therefore, the present invention discloses a preparation of a lanthanum carbonate co-precipitate which quickly disintegrates when placed in water, thus allowing for the development of an array of oral solid and liquid dosage forms of the drug.

Furthermore, this invention provides for a dosage form which is bioequivalent to the 500, 750, and 1000 mg doses of Fosrenol®, while utilizing a lower dose of elemental lanthanum.

The dosage forms disclosed herein are fairly stable to moisture gain and loss. The final moisture content is controlled by the preparative method utilized, and drying to a specified level is not required.

In accordance with the objectives of the present invention, applicants have developed a process for producing lanthanum carbonate oral dosage forms through co-precipitating air dried lanthanum carbonate hydrate. This co-precipitate, when compressed into tablet form, disintegrates quickly in water and therefore allows for the development of an array of oral dosage forms. These dosage forms include, but are not limited to, oral solutions, elixirs, tablets, capsules, sprinkles, granules, and dry powders.

In accordance with another embodiment of the present invention, disintegrants may be used as an additive in the lanthanum carbonate-containing co-precipitate.

DETAILED DESCRIPTION

The present invention is a lanthanum carbonate oral dosage form prepared by air drying lanthanum carbonate hydrate and then co-precipitating this material with an excipient. As disclosed herein, "co-precipitating" describes the process of rapidly removing water from a mixture such that the remaining material precipitates instead of crystallizing. Co-precipitation can be executed by methods known in the art including lypholization and spray-drying and can be done in the presence of a saccharide, pentahydric, or hexahydric alcohol, including mannitol or lactose. Many co-precipitation techniques are available, including lypholization and spray-drying which are disclosed herein as non-limiting examples. This co-precipitation process results in material of small particle size that is fairly stable to moisture gain and loss, retains phosphorous binding capacity, and rapidly and completely disintegrates when introduced to water.

The lanthanum carbonate ($La_2(CO_3)_3$) used in the present invention is in its hydrated form ($La_2(CO_3)_3 \cdot xH_2O$), and contains anywhere from four to fifteen moles of water (wherein x=4-15). The air-dried lanthanum carbonate hydrate used herein as a synthetic starting material can be prepared by either of the methods described in U.S. Pat. No. 5,968,976, although other methods known in the art may also be used.

The amount of elemental lanthanum used in the formulation ranges from 100 to 1000 mg. In preferred embodiments, the amounts of elemental lanthanum used include 250 to 700 mg. Lower doses of elemental lanthanum carbonate are also possible while retaining bioequivalence to higher doses of the commercially available 500, 750, and 1000 mg Fosrenol® chewable tablets. Although any complex or salt of elemental lanthanum, including both lanthanum carbonate and lanthanum hydroxy carbonate can be used, all dosage ranges are based on amounts of elemental lanthanum.

A tabletting excipient is mixed with the lanthanum carbonate hydrate described above prior to co-precipitation. Suitable tabletting excipients include, but are not limited to, saccharides, and pentahydric or hexahydric alcohol. In one embodiment, mannitol is the tabletting excipient. As a sugar derivative and osmotic diuretic agent, the excipient mannitol is known to be non-hygroscopic after lypholization. In another embodiment of the invention, lactose is used as the tabletting excipient. Other embodiments of the invention include the use of other pharmaceutical tabletting agents known to those skilled in the art, such as those agents described in *The Handbook of Pharmaceutical Excipients*.

In another embodiment of the invention, a disintegrant is also added to the lanthanum carbonate hydrate-excipient mixture prior to co-precipitation. Disintegrants are well-known excipients to those of skill in the art. In one embodiment, colloidal silicon dioxide or silicon dioxide is the disintegrant. These disintegrants are highly effective in allowing for efficient disintegration of the lyophilized dosage form. Other embodiments of the invention include, but are not limited to, the use of disintegrants such as mannitol/sorbitol blends, calcium silicate, a sodium starch glycolate and sodium carboxymethyl starch blend, colloidal $SiO_2$, a co-processed excipient system allowing for rapid disintegration such as that currently marketed by SPI Polyols Inc. as Pharmaburst™, silicified microcrystalline cellulose such as that currently marketed by FMC Corporation as Avicel®, sodium starch glycolate and sodium carboxymethyl starch blend such as that currently marketed by J. Rettenmaier & Söhne as ExploTab®, croscarmellose sodium such as that currently manufactured by Seppic as Ac-Di-Sol®, and ion-exchange resins such as that currently manufactured by Rohm and Haas Co. as Amberlite™.

Preferably, use of colloidal silicon dioxide or silicon dioxide such as that currently marketed by Huber as RxCIPIENTS®, FM-1000 is used as the disintegrant. The Huber material contains $CaSiO_4$ plus a smaller amount of $CaSO_4$ and is marketed for use in fast-disintegrating oral dosage formulations.

The amount of tabletting excipient used in the formulation ranges from about 100 to about 1000 mg. In preferred embodiments, the amounts of tabletting excipient used range from about 100 to about 750 mg. Varying ratios of lanthanum carbonate hydrate to the tabletting excipient are acceptable. Such ratios may vary from about 0.1 to about 10. In a preferred embodiment a 1:1 ratio of lanthanum carbonate hydrate to tabletting excipient is used.

The amount of disintegrant used in the formulation ranges from 0 to 25% based upon the weight of lanthanum carbonate. In preferred embodiments, the amounts of disintegrant used include 0 to 15% on the same basis. Varying ratios of lanthanum carbonate hydrate to the tabletting excipient to the disintegrant are acceptable. Generally, these ratios range from about 1-75: 1-75: 0-34. Preferably, they range from about _25-75: 25-75: 2-25. In a most preferred embodiment the ratio of lanthanum carbonate hydrate to excipient to disintegrant is about 50:50:10.

The lanthanum carbonate hydrate-excipient mixture or the lanthanum carbonate hydrate-excipient-disintegrant mixture then undergoes co-precipitation, such as by lyophilization or by spray-drying. Upon co-precipitating the lanthanum carbonate hydrate mixture, excess water is removed, which allows for the formation of a lanthanum carbonate co-precipitate. This lanthanum carbonate co-precipitate most likely contains some reproducible, although undetermined amount of water, either as hydrated lanthanum carbonate or otherwise. Furthermore, this complex is fairly stable when left open to air and does not absorb a significant amount of additional moisture.

The lanthanum carbonate co-precipitate can be further compressed into an appropriate pharmaceutical dosage forms with the incorporation of optional excipients such as disintegrants, glidants and lubricants. Such forms include, but are not limited to, tablets, capsules, and sprinkles. In a preferred embodiment, the co-precipitate is compressed into tablets that can readily be chewed, swallowed whole or easily dispersed in water or juice and then ingested.

The size and shape of the solid oral dosage form is not critical since the quick and complete disintegration property of this formulation provides the lanthanum carbonate as finely dispersed particles with a larger surface area than previous formulations of this drug. Therefore, a smaller dose of lanthanum carbonate may be employed. In one embodiment the tablets containing lanthanum carbonate are less than 22 mm round in diameter. In a preferred embodiment, the tablets of the same strength are less than 18 mm round in diameter.

In accordance with the invention, all of the formulations described herein are suitable for the treatment of a patient with hyperphosphatemia. Use of the described formulations of dried lanthanum carbonate hydrate has a phosphate binding capacity comparable or superior to that of Fosrenol® while allowing oral administration to a patient in a form other than a chewable tablet.

In accordance with a further embodiment, a pharmaceutical dosage form containing lanthanum carbonate comprises a product prepared by lyophilization or spray-drying of a mixture of $La_2(CO_3)_3$ or a hydrate thereof, an excipient such as colloidal silicon dioxide, silicon dioxide, starch, or povidone, preferably mannitol, and an optional disintegrant such as colloidal silicon dioxide, silicon dioxide, starch, or povidone, preferably colloidal silicon dioxide. The lanthanum carbonate, excipient, and disintegrant are mixed in a ratio of 1-75:1-75:0-34, preferably 5:3-5:0-2. The lanthanum carbonate may be hydrated to a water content of from about 4 to 15 moles of water per mole of lanthanum carbonate, preferably 8 to 14 moles of water. In various embodiments, the hydrated lanthanum carbonate may be air-dried to a water content of from about 6 to 11 moles of water per mole of lanthanum carbonate, preferably 8 moles of water. The dosage form has a disintegration time in water of from about 195 to 400 seconds and a phosphate binding capacity of between about 3.4 and about 4.6 mmol/g. The pharmaceutical dosage form may be made by mixing the lanthanum carbonate with the excipient and the optional disintegrant prior to coprecipitation. In various embodiments, 100 to 1000 mg of the lanthanum carbonate hydrate is coprecipitated with 100 to 1000 mg of the excipient and 0-25 wt. % of the disintegrant, based on the weight of the lanthanum carbonate.

The superior and unexpected properties of these lanthanum carbonate formulations is attributed to the ability of the claimed formulations to disintegrate and provide lanthanum carbonate with high surface area as compared to the previously described lanthanum carbonate hydrates. Examples herein are disclosed to provide a better understanding of the invention, but do not limit the invention in any manner.
The following examples further illustrate the invention and its unique characteristics. These examples are not intended to limit the invention in any manner.

Examples 1-8

General Procedure for Preparing a Co-Precipitate Via Lypholization

Mannitol (6.5 g) was dissolved in 200 mL deionized water in a 600 mL lypholization flask. An optional disintegrant, such as colloidal $SiO_2$ (650 mg) was added, followed by 6.5 g of $La_2(CO_3)_3 \cdot 8H_2O$. The mixture was swirled while quickly frozen in a dry ice/acetone (−78° C.) bath. It was then placed under vacuum and lyophilized for 2-3 days until free of ice particles. The resultant fluffy white compounds were collected.

| Example | Composition | Ratio |
|---|---|---|
| 1 | $La_2(CO_3)_3$ hydrate/Mannitol | 1:1 |
| 2 | $La_2(CO_3)_3 \cdot$hydrate/Mannitol/$SiO_2$ | 1:1:0.1 |
| 3 | | 1:1:0.2 |
| 4 | | 1:1:0.4 |
| 5 | $La_2(CO_3)_3$ hydrate/Mannitol/ | 1:1:0.1 |
| 6 | Calcium silicate | 1:1:0.2 |
| 7 | | 1:1:0.4 |
| 8 | $La_2(CO_3)_3$ hydrate/Colloidal $SiO_2$ | 1:1:0.2 |

Examples 9-13

General Procedure for Preparing a Co-Precipitate Via Spray-Drying

A mixture of lanthanum carbonate octahydrate (13.4 g), mannitol (12.1 g), and FM-1000 (4.8 g) was stirred in 500 mL deionized water in an Ehrlenmeyer flask. After a few minutes, the solution was sieved through a 250 μM mesh screen. The solution was then stirred while running through an SD-Micro Spray Dryer (GEA Niro Inc.). The conditions used were 150° C. inlet temperature; 75° C. outlet temperature; spray rate of 2.5 kg/min; 30 kg/hr drying gas flow; and 1.5 bar nozzle pressure. The fluffy white compounds were collected.

| Example | Composition | Ratio |
|---|---|---|
| 9 | $La_2(CO_3)_3$ hydrate/Mannitol | 1:1 |
| 10 | $La_2(CO_3)_3$ hydrate/Mannitol/Calcium silicate | 1:1:0.4 |
| 11 | $La_2(CO_3)_3$ hydrate/Lactose/Starch | 50:40:10 |
| 12 | $La_2(CO_3)_3$ hydrate/Lactose/Sodium starch glycoloate and sodium carboxymethyl starch blend | 50:47:3 |
| 13 | $La_2(CO_3)_3$ hydrate/Lactose/$SiO_2$/Croscarmellose sodium | 50:30:10:10 |

Examples 14-17

Plain Lanthanum Carbonate Hydrates

Plain lanthanum carbonate hydrates (Examples 14-16) were prepared and analyzed for moisture content according to U.S. Pat. No. 5,968,976. Fosrenol® tablets, containing lanthanum carbonate tetrahydrate and/or pentahydrate as the active ingredient, were also purchased and analyzed.

| Example | Composition |
|---|---|
| 14 | $La_2(CO_3)_3 \cdot 5H_2O$ |
| 15 | $La_2(CO_3)_3 \cdot 8H_2O$ |
| 16 | $La_2(CO_3)_3 \cdot 14H_2O$ |
| 17 (Fosrenol ®) | $La_2(CO_3)_3 \cdot 4\text{-}5H_2O$ |

The uncoated, compressed tablets were assessed for disintegration. Table I gives the disintegration times for the whole, intact tablets in deionized water. The disintegration time was measured using the procedure and apparatus as described by physical test <701>, Disintegration, from The United States Pharmacopeia, Volume 29. The disintegration of a single tablet from each example was measured.

TABLE I

Disintegration Data for Co-Precipitated Compositions and Prior Art Compositions

| Example | Composition | Ratio | Disintegration Time |
|---|---|---|---|
| 1 (lyophilized) | $La_2(CO_3)_3$ hydrate/ | 1:1 | 400 sec |
| 9 (spray-dried) | Mannitol | | 270 sec |
| 2 | $La_2(CO_3)_3$ | 1:1:0.1 | 330 sec |
| 3 | hydrate/ | 1:1:0.2 | 255 sec |

TABLE I-continued

Disintegration Data for Co-Precipitated Compositions and Prior Art Compositions

| Example | Composition | Ratio | Disintegration Time |
|---|---|---|---|
| 4 | Mannitol/$SiO_2$ | 1:1:0.4 | 270 sec |
| 5 | $La_2(CO_3)_3$ hydrate/ | 1:1:0.1 | 240 sec |
| 6 |  | 1:1:0.2 | 210 sec |
| 7 (lyophilized) | Mannitol/FM-1000 | 1:1:0.4 | 195 sec |
| 10 (spray-dried) |  |  | 270 sec |
| 8 | $La_2(CO_3)_3$ hydrate/ Pharmaburst | 1:1 | 240 sec |
| 11 | $La_2(CO_3)_3$ hydrate/ Lactose/Starch | 50:40:10 | 36 min |
| 12 | $La_2(CO_3)_3$ hydrate/ Lactose/Explotab | 50:47:3 | 19 min |
| 13 | $La_2(CO_3)_3$ hydrate/ Lactose/$SiO_2$/AcDiSol | 50:30:10:10 | 260 sec |
| 14 | $La_2(CO_3)_3 \cdot 5H_2O$ |  | 5 hours |
| 15 | $La_2(CO_3)_3 \cdot 8H_2O$ |  | >7 hours |
| 16 | $La_2(CO_3)_3 \cdot 14H_2O$ |  | >7 hours |
| Fosrenol ® | $La_2(CO_3)_3 \cdot 4\text{-}5H_2O$ (active ingredient) |  | 6 hours |

It can be seen from Table I that all of the lyophilized and spray dried complexes 1-13 of this invention showed significant improvement over the prior art lanthanum carbonate complexes of Examples 14-17. Complexes 1-13 were unexpectedly uniform in their disintegration, with the exception of complexes 11 and 12. However, the disintegration time of the compositions of Examples 11 and 12 were still only a fraction of those of the prior art compositions. Very little difference was observed between these compositions, even though the percentage (w/w) of disintegrant varied from no added disintegrant to as much as 40% based on the weight of the starting lanthanum carbonate octahydrate (this is 87% based on the weight of elemental lanthanum). The preparation of complexes by lypholization vs. spray-drying also had little effect. Most of these complexes completely disintegrated within 6 minutes.

To rule out the possibility that the enhanced disintegration profile could arise solely from the addition of excipients to lanthanum carbonate, Fosrenol® tablets were also analyzed. The inactive ingredients in Fosrenol® are dextrates, colloidal $SiO_2$, and magnesium stearate. However, the Fosrenol® tablets showed equally poor disintegration as the lanthanum carbonate hydrates of Examples 14-16.

Table II describes the phosphate binding ability of the prepared Examples in either whole or ground tablet form. The ground tablets simulate a chewable tablet formulation after chewing has occurred. Phosphate binding ability is a term used to predict the amount of phosphate that can be bound by a sequestrant under conditions which employ a large excess of phosphate, such as those found in the stomach. Mazzeo, J. R.; et. al. *Journal of Pharmaceutical and Biomedical Analysis* 1999, vol. 19, pps. 911-915. This assay, which utilizes a large excess of phosphate, is therefore a better functional model of biological conditions than the assay described in U.S. Pat. No. 5,968,976 which utilizes only two molar equivalents of phosphate ion per mole of lanthanum carbonate.

The uncoated, compressed tablets obtained from Examples 1-17 were assessed for phosphate binding ability. Whole tablets, prepared as described above, as well as coarsely ground tablets were both examined.

Phosphate Binding Assay i. Preparation of stock phosphate solution:

21.4 g N,N-bis(hydroxyethyl)-2-aminoethanesulfonic acid, 4.7 g NaCl, and 2.7 g $KH_2PO_4$ (ultra high purity) were added to a 1000 mL volumetric flask and dissolved in 950 mL DI $H_2O$. The pH was then adjusted to 3.0 (±0.05) with HCl, and the solution was diluted to volume with DI $H_2O$ and mixed.

ii. Assay:

The lanthanum carbonate complex was added to the stock phosphate solution so that the final concentration was 2.5 mg $La_2(CO_3)_3$/mL phosphate solution. The mixture was heated at 37° C. for 60 minutes with constant swirling. It was then filtered through a 0.2 µm nylon filter.

The sample was then diluted to allow injection into the ion chromatograph. Here, a dilution factor of 100 was used: a 1.0 mL aliquot was removed and diluted volumetrically to 100 mL with DI water.

iii. Phosphate Measurement

The amount of unbound phosphate was determined by ion chromatography on a Dionex ICS-1500 ion chromatograph equipped with a conductivity cell (35° C.) and a Dionex MRS 300 4 mm auto suppressor. Material was eluted through a Dionex AG11-HC guard column (4×50 mm) and a Dionex AS11-HC column (4×250 mm) at 1.0 mL/min using 25 mM NaOH in DI $H_2O$ as the mobile phase. The sample response was then recorded by a computerized chromatography data system.

iv. Construction of Phosphate Calibration Curve

The linearity of the response was verified as follows. A series of standards over a wide range of free phosphate concentration (approximately 0.04, 0.06, 0.10, 0.15, 0.20, and 0.25 mM) were prepared and their ion chromatographic responses were determined. A plot of free phosphate concentration (mM) vs. response was then constructed. The slope and y-intercept of the resulting linear regression plot were then determined.

The phosphate binding capacity was calculated from the following equations.

$$\text{Unbound Phosphate Concentration (mM)} = \frac{\text{Sample Response}}{\text{Standard Response}} \times \text{Dilution Factor}$$

$$\text{Phosphate Binding Capacity (mmol/g)} = \frac{(\text{Conc. of stock phosphate soln. (mM)} - \text{Unbound Phosphate Conc. (mM)}) \times \text{Volume of Phosphate Solution (L)}}{\text{Weight of Lanthanum Carbonate (La}_2\text{(CO}_3\text{)}_3\text{ (g) in complex}}$$

TABLE II

Binding Capacity Data for Co-Precipitated and Prior Art Compositions

| | | | Binding Capacity (mmol $PO_{4-2}$/g $La_2(CO_3)_3$) | |
|---|---|---|---|---|
| Example | Composition | Ratio | Ground Tablet | Whole Tablet |
| 1 (lyophilized) | $La_2(CO_3)_3$ hydrate/ Mannitol | 1:1 | 3.9 | 3.7 |

TABLE II-continued

Binding Capacity Data for Co-Precipitated and Prior Art Compositions

| Example | Composition | Ratio | Binding Capacity (mmol $PO_4{}^{-2}$/g $La_2(CO_3)_3$) Ground Tablet | Binding Capacity (mmol $PO_4{}^{-2}$/g $La_2(CO_3)_3$) Whole Tablet |
|---|---|---|---|---|
| 9 (spray-dried) | | | 4.3 | 4.4 |
| 2 | $La_2(CO_3)_3$ hydrate/ Mannitol/$SiO_2$ | 1:1:0.1 | 3.5 | 3.7 |
| 3 | | 1:1:0.2 | 3.3 | 3.7 |
| 4 | | 1:1:0.4 | 4.3 | 4.0 |
| 5 | $La_2(CO_3)_3$ hydrate/ Mannitol/FM-1000 | 1:1:0.1 | 3.6 | 3.9 |
| 6 | | 1:1:0.2 | 3.8 | 3.9 |
| 7 | | 1:1:0.4 | 3.0 | 3.4 |
| (lyophilized) | | | | |
| 10 (spray-dried) | | | 4.5 | 4.6 |
| 8 | $La_2(CO_3)_3$ hydrate/ Pharmaburst | 1:1:0.2 | 3.6 | 3.4 |
| 11 | $La_2(CO_3)_3$ hydrate/ Lactose/Starch | 50:40:10 | 4.4 | 4.4 |
| 12 | $La_2(CO_3)_3$ hydrate/ Lactose/Explotab | 50:47:3 | 4.4 | 4.4 |
| 13 | $La_2(CO_3)_3$ hydrate/ Lactose/$SiO_2$/AcDi Sol | 50:30:10:10 | 4.1 | 4.1 |
| 14 | $La_2(CO_3)_3 \cdot 5H_2O$ | | 3.0 | 0.7 |
| 15 | $La_2(CO_3)_3 \cdot 8H_2O$ | | 3.0 | 0.6 |
| 16 | $La_2(CO_3)_3 \cdot 14H_2O$ | | 3.6 | 0.8 |
| 17 | Fosrenol ® | | 1.9 | 0.4 |

Ground Tablet = A whole tablet was coarsely ground before analysis. Whole Tablet = A whole tablet, without further modification, was used.

The data in Table II clearly demonstrates that the co-precipitates of the instant invention are suitable for use in whole tablet form. While Examples 1-13 show essentially the same binding ability in either the form of a ground or a whole tablet, Examples 14-16 lose significant amounts of binding ability as whole tablets. Thus, dosage forms of the claimed compositions such as tablets, capsules, powders, sprinkles, or granules can be used. These materials may also be dispersed in a liquid, such as in an oral solution or an elixir, to facilitate dosing to patients unable or unwilling to swallow a solid oral dosage form.

Most surprisingly, the co-precipitates of the invention consistently display phosphate binding ability that is as much as twice as high as the marketed Fosrenol® tablets. Therefore, the use of these co-precipitates would allow a much smaller dose to be used to achieve the same amount of phosphate removal.

The invention, although described in specific embodiments above, encompasses numerous variations on the formulation and freeze-drying or spray-drying techniques. The embodiments, as outlined above, are intended to be illustrative of the invention and not to limit the formulation and principles in any way.

What is claimed is:

1. A rapidly disintegrable pharmaceutical dosage form comprising co-precipitated lanthanum carbonate, wherein said lanthanum carbonate is prepared by coprecipitation with an excipient and an optional disintegrant, wherein the excipient is selected from the group consisting of a saccharide, a pentahydric alcohol, a hexahydric alcohol and a mixture thereof;
   said coprecipitation comprising freezing an aqueous mixture comprising said lanthanum carbonate, said excipient and said optional disintegrant to produce a frozen mixture; and
   lyophilizing said frozen mixture under vacuum.

2. The pharmaceutical dosage form of claim 1 wherein the excipient is present in a 1:1 ratio with the lanthanum carbonate.

3. The pharmaceutical dosage form of claim 1, comprising 100 to 1000 mg of the lanthanum carbonate, 100 to 750 mg of the excipient and 0-25 wt. % of the disintegrant, based on the weight of the lanthanum carbonate.

4. The pharmaceutical dosage form of claim 1 wherein the disintegrant is selected from the group consisting of colloidal silicon dioxide, silicon dioxide, starch, and povidone.

5. The pharmaceutical dosage form of claim 1, wherein the lanthanum carbonate is hydrated and has the general formula: $La_2(CO_3)_3 \cdot xH_2O$, wherein x has a value of 4-15.

6. The pharmaceutical dosage form of claim 1, wherein a ratio of the lanthanum carbonate to the excipient to the disintegrant is 25-75: 25-75: 2-25.

7. The pharmaceutical dosage form of claim 6, wherein the ratio is 40-50:40-50:10-20.

8. The pharmaceutical dosage form of claim 1, said dosage form being compressed into an oral solid form.

9. The pharmaceutical dosage form of claim 8, wherein the oral solid form is adapted to be dissolved into a liquid form prior to ingestion by the patient.

10. The pharmaceutical dosage form of claim 9, wherein the dosage form disintegrates in between 2 and 20 minutes.

11. The pharmaceutical dosage form of claim 9, wherein the dosage form has a phosphate binding capacity of between 2.5 and 5 mmol/g.

12. A method of treating hyperphosphataemia with the pharmaceutical dosage form of claim 1.

13. A method of treating hyperphosphataemia according to claim 12, wherein the dosage form is a tablet which is adapted to be dissolved in a liquid prior to administration.

14. A pharmaceutical dosage form comprising a product prepared by lyophilization of a mixture of $La_2(CO_3)_3$, Mannitol, and colloidal $SiO_2$ in a ratio of 1-75:1-75:0-34;
   wherein the lanthanum carbonate is hydrated to a water content of between about 6-11 moles of water, and the dosage form has a disintegration time of from about 195 to 400 seconds and a phosphate binding capacity of between about 3.4 and about 4.6 mmol/g.

15. The dosage form of claim 14, wherein the ratio is 5:3-5:0-2.

16. A process for preparing a rapidly disintegrating pharmaceutical dosage form comprising co-precipitating lanthanum carbonate hydrate with an excipient and an optional disintegrant by lyophilization,
   wherein the excipient is selected from the group consisting of a saccharide, a pentahydric alcohol, a hexahydric alcohol, and a mixture thereof,
   wherein said coprecipitation comprises freezing an aqueous mixture comprising said lanthanum carbonate, said excipient and said optional disintegrant to produce a frozen mixture; and
   lyophilizing said frozen mixture under vacuum.

17. The process of claim 16, wherein 100 to 1000 mg of the lanthanum carbonate hydrate is coprecipitated with 100 to 1000 mg of the excipient and 0-25 wt. % of the disintegrant, based on the weight of the lanthanum carbonate.

18. The process of claim 16, wherein the disintegrant is selected from the group consisting of colloidal silicon dioxide, silicon dioxide, starch, and povidone.

19. The process of claim 16 wherein the hydrated lanthanum carbonate has the general formula: $La_3(CO_3)_3 \cdot xH_2O$, wherein x has a value of 4-15.

20. The method of claim 16 wherein a ratio of the lanthanum carbonate to the excipient is 1:1.

21. The process of claim 16 wherein the composition is compressed into an oral solid form following coprecipitation.

22. A rapidly disintegrable pharmaceutical dosage form comprising coprecipitated lanthanum carbonate, wherein said lanthanum carbonate is prepared by coprecipitation with an excipient and an optional disintegrant;
   wherein said coprecipitation consists of spray-drying an aqueous mixture consisting of said lanthanum carbonate, said excipient and said optional disintegrant;
   said excipient being selected from the group consisting of pentahydric alcohols, hexahydric alcohols, lactose, and mixtures thereof; and
   said disintegrant being selected from the group consisting of colloidal silicon dioxide, silicon dioxide, calcium silicate, sodium starch glycolate, sodium carboxymethyl starch, carboxymethyl cellulose, povidone, and mixtures thereof.

23. A process for preparing a rapidly disintegrable pharmaceutical dosage form according to claim 22, said method comprising:
   spray-drying said aqueous mixture consisting of said lanthanum carbonate, said excipient and said optional disintegrant.

* * * * *